(12) United States Patent
Ishikawa et al.

(10) Patent No.: US 9,663,776 B2
(45) Date of Patent: May 30, 2017

(54) XYLANASE

(71) Applicant: NATIONAL INSTITUTE OF ADVANCED INDUSTRIAL SCIENCE AND TECHNOLOGY, Tokyo (JP)

(72) Inventors: Kazuhiko Ishikawa, Higashi-hiroshima (JP); Hiroyuki Inoue, Higashi-hiroshima (JP)

(73) Assignee: NATIONAL INSTITUTE OF ADVANCED INDUSTRIAL SCIENCE AND TECHNOLOGY, Tokyo (JP)

(*) Notice: Subject to any disclaimer, the term of this patent is extended or adjusted under 35 U.S.C. 154(b) by 0 days.

(21) Appl. No.: 14/436,573

(22) PCT Filed: Oct. 18, 2013

(86) PCT No.: PCT/JP2013/078256
§ 371 (c)(1),
(2) Date: Apr. 17, 2015

(87) PCT Pub. No.: WO2014/061763
PCT Pub. Date: Apr. 24, 2014

(65) Prior Publication Data
US 2015/0284699 A1 Oct. 8, 2015

(30) Foreign Application Priority Data
Oct. 19, 2012 (JP) .................................. 2012-231592

(51) Int. Cl.
*C12N 9/24* (2006.01)
*C12P 19/02* (2006.01)
*C12P 19/12* (2006.01)
*C12P 19/14* (2006.01)
*C12N 9/42* (2006.01)

(52) U.S. Cl.
CPC ........... *C12N 9/248* (2013.01); *C12N 9/2434* (2013.01); *C12P 19/02* (2013.01); *C12P 19/12* (2013.01); *C12P 19/14* (2013.01); *C12Y 302/01008* (2013.01)

(58) Field of Classification Search
None
See application file for complete search history.

(56) References Cited

U.S. PATENT DOCUMENTS

| 5,658,765 A | 8/1997 | Noguchi et al. | |
| 6,534,101 B1* | 3/2003 | Sabatier | C12N 9/18 |
| | | | 426/18 |
| 2010/0136618 A1* | 6/2010 | Fang | C12P 19/14 |
| | | | 435/69.1 |

FOREIGN PATENT DOCUMENTS

| JP | 06-261750 | 9/1994 |
| JP | 2001-017180 | 1/2001 |
| JP | 2002-513595 | 5/2002 |
| WO | 99/57325 | 11/1999 |
| WO | 2007/146944 | 12/2007 |
| WO | 2010/072224 | 7/2010 |
| WO | 2010/072225 | 7/2010 |
| WO | 2010/072226 | 7/2010 |

OTHER PUBLICATIONS

Furniss, C. et al., A family 11 xylanase from Penicillium funiculosum is strongly inhibited by three wheat xylanase inhibitors, Biochimica et Biophysica Acta 2002, vol. 1598, No. 1-2, pp. 24-29.
Watanabe, M. et al., Xylanase (GH11) from Acremonium cellulolyticus: homologous expression and characterization, AMB Express 2014, 4:27.
International Search Report for PCT/JP2013/078256, dated Jan. 21, 2014, and English translation.

* cited by examiner

Primary Examiner — Suzanne M Noakes
(74) Attorney, Agent, or Firm — Wenderoth, Lind & Ponack, L.L.P.

(57) ABSTRACT

The purpose of the present invention is to provide a novel xylanase having various excellent enzymological properties, and that is suitable for industrial applications. The polypeptide is selected from the group consisting of (a), (b), and (c) below: (a) a polypeptide comprising an amino acid sequence selected from SEQ ID NOs: 1 to 7; (b) a polypeptide having xylanase activity and comprising an amino acid sequence selected from SEQ ID NOs: 1 to 7, the amino acid sequence having substitution, deletion, insertion, and/or addition of one or several amino acid residues; and (c) a polypeptide having xylanase activity and comprising an amino acid sequence having at least 80% identity with an amino acid sequence selected from SEQ ID NOs. 1 to 7.

6 Claims, 4 Drawing Sheets

Fig. 6

```
XYLC        -------MFPSGLTQ--------------------HATGDLSKRQSITTSQTGTNN----  29
XYLF        MFSFSTAFFASTLAAGILASPA------------AAPSALTKRN--TPNSSGTNN----  41
XYLE        MIYFPQLMVVLTAIHSAIAVPTGQTQAS----VQKRGPHNFVMGPDHPLMMARRNESLFR  56
XYLG        MVAFSSLFTALAAIAGSLAAPADLVKNDNVPDLGSRGPSNFVIDTTNNTSLARRS-----  55
XYLB        -MGISSILLSALIAGGALALPA------------AEPVSFDIR-DENITLARRAE----  41
XYLA        -MKITSVFAGLLAT--ALAAPV------------------EDSALVERAG----        29
XYLD        MRSFARLVFSLLPVIGALAVPATSDNHARYLDMASRSADFRQRIRDMIANATQENDISKR  60
                          .

XYLC        --------------GYYYSFWTNGG-GEVTYTNG-DNGEYSVTWVN--CGDFTSGKGWNPA  72
XYLF        --------------GFFYQFWDDGSSGTTTYTNG-PAGEYSVNWQN--VGDFTAGKGWSQA  85
XYLE        --------------RATNYIQDYTTGGT-VDFSP--ESGEFSLSWDT--TDDFVVGVGWNPG  99
XYLG        --------------AINYDQDYTTGGT-VNYYS--SSTGFEVTWNT--QDDFVVGVGWNPG  97
XYLB        --------------AINYNQNYIASGANVQYSPNIAAGSFSINYNT--QGDFVVGLGWQPG  86
XYLA        --------------GINYVQNYNGNLG--DFTYNESAGTYSMYWEDGVNGDFVVGLGWSTG  74
XYLD        DSVFSTSKDGVDSAGFYYSLYNDNHASAGYTEFSDSGRFEVGWNLASSSEFLGGKGYRDT  120
                          .  *        .     :            :.: :      .:*  * *:

XYLC        NAQTVTYSGEFNTS-GNAYLAVYGWTTDPLVEYYILESYGTYNPSSGLTLLGQVTSDGGT  131
XYLF        EPRNISFSGSVNCG-GNFYLAVYTWSTQ--GENYILEDYGTYNPCSGGTSKGSLYSDGSE  142
XYLE        STEPITHSGSFNVESGLASLSVYGWTTNPLVEYYIIDEYVNM-EQAGTQ-KGTVYSDGAT  157
XYLG        STTPINFGGQFSVSSGTGLLSVYGWSTSPLVEYYIIEDYANP-PSFGTQ-KGSLTSDGGT  155
XYLB        DANPITYSGSFSAS-GVGILAVYGWTTNPLVEYYIMEVHDGY-QTVGTH-KGTVTSDGGT  143
XYLA        AARSITYSANYNAANSGSYLSVYGWINSPQAEYYIVENYGNYNPCSGAQSLGTLTSDGGT  134
XYLD2       KTRCSLTWDGYFTATGDYTLAIYGWTLNPVTEWYIVEQHGTGTPGNGNV-RGTITSDGGT  179
                              .      *::*  *  .    *  **::  :          *      *  :  ***.

XYLC        YDIYSTQRVDQPSIEGTSTFNQYWSVRTEKRVGGTVTTANHFAAWKALGLEMGTYN---Y  188
XYLF        YQVCLVDRGNN--------YLQNWSVRQNKRTSGTVTTANHYNYYQSQGMNHNPLSSAVY  194
XYLE        YTIWENQRVNEPSIEGTSTFNQYISIRESNRASGTITVENHFNAWANVGLKLGTMD---F  214
XYLG        YIIWENTRYNEPSIQGTSTFNQYISVRQSPRTEGTVTVQNHFNAWKNLGMNLGTLN---F  212
XYLB        YDIWEHQQVNQPSILGTSTFNQYISIRQSPRTSGTVTVQNHFNAWAQAGLNLGTMN---Y  200
XYLA        YQVCTDTRYNQPSITGTSTFTQFFSVRQNKRSSGTVTTGNHFNFWAQHGFGN-SYN---F  190
XYLD        YDVYDLYYSNVPSIYGVTSFHQYWSIRNVGRSTGTVDVTKHFDTWKSLGLNPGTPI---F  236
             * :       :           :*   *:*    *   **:   . :*:    *:      .   :

XYLC        MIVSTEGYESSGSSTITVS-----------------------------------------  207
XYLF        QIVSTEGYGSSGSADITVSEASPSTSSSASTTSSTSPATTSSSSGTGASQWGQCGGIGWN  254
XYLE        QVIAVESWDGSGNAQQTATQ-----------------------------------------  234
XYLG        QVIAAEGWGGSGSASYAVNNN----------------------------------------  233
XYLB        QVLAVESWSGSGSGQISLSKGTGGGTTTTTPTGPTSTSTAPSSGGTGAAQWGQCGGIGWT  260
XYLA        QVMAVEAFNGAGSATVTVS-----------------------------------------  209
XYLD        QMVTLEGFKGQGYLDFTVS-----------------------------------------  255
                  ::: *.: . *   : .

XYLC        ---------------------
XYLF        GPTTCVSPYTCQQINPYYYQCL  276
XYLE        ---------------------
XYLG        ---------------------
XYLB        GPTTCVSPYTCKYFNAYYSQCQ  282
XYLA        ---------------------
XYLD        ---------------------
```

XYLANASE

TECHNICAL FIELD

The present invention relates to xylanase, its gene, and the use thereof.

BACKGROUND ART

Xylan is one of the ubiquitous, naturally occurring polysaccharides, and is a major constituent of plants. From a structural viewpoint, xylan is a macromolecular polysaccharide containing a main chain made from units of xylose, which is polymerized by β-1,4 xyloside linkage. Xylan is present in nature not only as a homoxylan consisting of only xylose, but also as a heteroxylan such as arabinoxylan containing branched arabinose attached to the main chain.

Xylanase is a generic term for a group of enzymes that hydrolyze xylan, and that are widely found in animals, plants, and microorganisms. There has been research largely focusing on xylanase derived from bacteria, actinomycetes, yeast, fungi, and the like. Xylanase is used in production of xylooligosaccharides or xylose from xylan, as well as in biomass processing. In particular, xylanase has recently been brought to attention as being useful from the point of view of enzyme utilization in biomass processing. For example, xylanase is used in enzymatic degradation of agricultural waste for alcohol fuels, enzymatic treatment for liberating saccharides in animal feed, enzymatic treatment for dissolving pulp in the step of obtaining cellulose, and enzymatic treatment for bleaching wood pulp.

In the paper and pulp industry, recent years have seen increasing promise of using xylanase for improvement in whiteness and quality of pulp, reduction in the amount of chemical bleaching agents, such as chlorine bleaching agents, used in the pulp-bleaching step, and increase in pulp freeness in the paper-recycling step. Xylanase is also used in animal feed and in the food-processing field (Patent Document 1).

An object of the present invention is to provide a novel highly-active xylanase that is useful for applications, for example, in biomass decomposition, food processing, pulp bleaching, animal feed, and silage.

CITATION LIST

Patent Documents

Patent Document 1: JPH06-261750A

SUMMARY OF INVENTION

Technical Problem

In view of the state of the art, an object of the present invention is to provide a novel xylanase having various excellent enzymological properties, and that is suitable for industrial applications.

Solution to Problem

The present inventors conducted extensive research to achieve the above object, and succeeded in obtaining a novel polypeptide having sufficient xylanase activity even in a high-temperature environment, and a DNA that encodes the polypeptide. The present inventors further analyzed the 3D-structure of the enzyme, and identified the key amino acid that is present in the catalytic site. The present inventors also confirmed the presence of other gene clusters and gene fragments for encoding xylanase in the genomic DNA of an organism from which the polypeptide is derived, and found from this study that there are a plurality of novel xylanases. On the basis of these findings, the inventors conducted further research, and made improvements to complete the present invention.

The following is the major part of the present invention.

Item 1.

A polypeptide selected from the group consisting of (a), (b), and (c) below:

(a) a polypeptide comprising an amino acid sequence selected from SEQ ID NOs: 1 to 7;

(b) a polypeptide having xylanase activity and comprising an amino acid sequence selected from SEQ ID NOs: 1 to 7, the amino acid sequence having substitution, deletion, insertion, and/or addition of one or several amino acid residues; and (c) a polypeptide having xylanase activity and comprising an amino acid sequence having at least 80% identity with an amino acid sequence selected from SEQ ID NOs. 1 to 7.

Item 2.

A polynucleotide selected from the group consisting of (a), (b), and (c) below:

(a) a polynucleotide comprising a base sequence selected from SEQ ID NOs: 8 to 21;

(b) a polynucleotide comprising a base sequence that encodes an amino acid sequence selected from SEQ ID NOs. 1 to 7; and (c) a polynucleotide that hybridizes with a polynucleotide comprising a base sequence complementary to a base sequence selected from SEQ ID NOs. 8 to 21 under stringent conditions, and that encodes a polypeptide having xylanase activity.

Item 3.

An expression vector comprising the polynucleotide according to Item 2.

Item 4.

A transformant obtained by transformation with the expression vector according to Item 3.

Item 5.

A process for producing xylanase, the process comprising the step of culturing the transformant according to Item 4.

Item 6.

A process for producing xylose and/or xylobiose, the process comprising the step of allowing the polypeptide according to Item 1 to act on a sample containing xylan.

Advantageous Effects of Invention

The polypeptide according to the present invention, when allowed to act on a sample comprising xylan, can produce xyloses and/or xylooligosaccharides on an industrial scale because of its xylanase activity. In a preferred embodiment, the polypeptide according to the present invention is suitably used in an environment where the temperature changes or is at a relatively high temperature (e.g., 40 to 80° C.) because of its high specific activity and excellent thermal stability. Moreover, since the polynucleotide according to the present invention encodes the polypeptide according to the present invention, the polynucleotide, when expressed in an appropriate host, can efficiently produce a large amount of the polypeptide (i.e., xylanase).

BRIEF DESCRIPTION OF DRAWINGS

FIG. 6 shows the alignment of the amino acid sequences of seven xylanases encoded in respective genomic DNA. The amino acid sequence of XYLC is provided in SEQ ID NO:1. The amino acid sequence of XYLA is provided in SEQ ID NO:2. The amino acid sequence of XYLB is provided in SEQ ID NO:3. The amino acid sequence of XYLD is provided in SEQ ID NO:4. The amino acid sequence of XYLE is provided in SEQ ID NO:5. The amino acid sequence of XYLF is provided in SEQ ID NO:6. The amino acid sequence of XYLG is provided in SEQ ID NO:7.

DESCRIPTION OF EMBODIMENTS

1. Polypeptide Having Xylanase Activity

Figure 1:
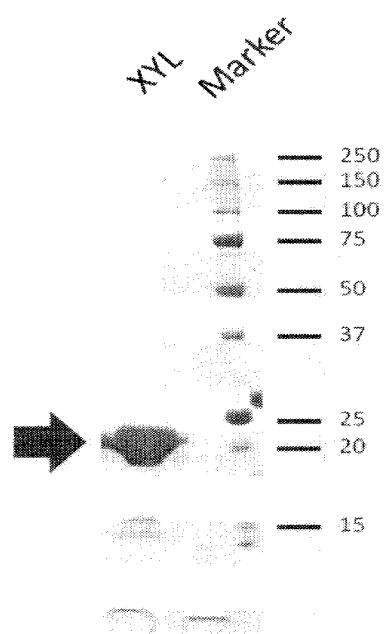
FIG. 1 shows the results of SDS-PAGE on the protein purified in Example 1.

The polypeptide according to the present invention is (a) a polypeptide comprising (an amino acid sequence selected from SEQ ID NOs: 1 to 7; (b) a polypeptide having xylanase activity and comprising an amino acid sequence selected from SEQ ID NOs: 1 to 7, the amino acid sequence having substitution, deletion, insertion, and/or addition of one or several amino acid residues; or (c) a polypeptide having xylanase activity and comprising an amino acid sequence having at least 80% identity with an amino acid sequence selected from SEQ ID NOs. 1 to 7.

The amino acid sequence of SEQ ID NO: 1 has been confirmed to have xylanase activity in the Examples described below. The results of structural analysis suggest that the glutamic acids residue at positions 119 and 210 of the amino acid sequence of SEQ ID NO: 1 correspond to the catalytic site, and these amino acids are conserved in the amino acid sequences of SEQ ID NOs: 2 to 7. The amino acid sequences around the amino acids at positions 119 and 210 are also highly conserved in amino acid sequences of SEQ ID NOs: 1 to 7. Furthermore, because the amino acid sequence of SEQ ID NO: 1 has identity of 37%, 42%, 35%, 37%, 47%, and 41% to amino acid sequences of SEQ ID NOs: 1 to 7, respectively, a polypeptide comprising an amino acid sequence selected from SEQ ID NOs: 1 to 7 is considered to have xylanase activity. The amino acid sequence of SEQ ID NO: 22 is an amino acid sequence of SEQ ID NO: 1 to which a signal peptide is added. Each of the amino acid sequences of SEQ ID NOs: 2 to 7 also has a signal peptide added to its N-terminus.

In the polypeptide (b) above, the term "several" is not particularly limited, insofar as the polypeptide has xylanase activity, or preferably has excellent temperature dependence. For example, the term "several" refers to 50, 45, 30, 25, 20, 15, 10, 5, 3, or 2. The presence or absence of xylanase activity can be confirmed by a known technique such as the Somogyi-Nelson method. Specific examples of polypeptide (b) include polypeptides comprising an amino acid sequence selected from SEQ ID NOs: 2 to 7, and 22.

When the mutation is the substitution of one or several amino acid residues, the type of substitution is preferably, but not particularly limited to, conservative amino acid substitution from the standpoint that the higher-order structure, phenotype, or properties of the polypeptide is not adversely affected in a significant manner. The term "conservative amino acid substitution" refers to substitution of an amino acid residue with another amino acid residue having a side chain of similar nature. Amino acid residues can be classified into families of similar nature according to their side chains, such as basic side chains (e.g., lysine, arginine, and histidine), acidic side chains (e.g., aspartic acid, and glutamic acid), uncharged polar side chains (e.g., glycine, asparagine, glutamine, serine, threonine, tyrosine, and cysteine), nonpolar side chains (e.g., alanine, valine, leucine, isoleucine, proline, phenylalanine, methionine, and tryptophan), β-branched side chains (e.g., threonine, valine, and isoleucine), and aromatic side chains (e.g., tyrosine, phenylalanine, tryptophan, and histidine). Thus, substitution of an amino acid residue is preferably made such that an original amino acid residue is substituted with an amino acid residue belonging to the same family as that of the original amino acid residue of the original amino acid sequence.

In the polypeptide (b), mutations such as substitution, deletion, insertion and/or addition, or the like of one or several amino acid residues are made preferably in the regions that are not significantly essential for the higher-order structure of the polypeptide, or in the regions that are not directly associated with its catalytic activity. Examples of such regions include the N-terminal domain, the C-terminal domain, and poorly conserved regions between SEQ ID NOs: 1 to 7. For example, the N-terminus and/or the C-terminus may have a signal sequence added thereto. Examples of signal sequences include, but are not particularly limited to, those consisting of 3 to 50, preferably 5 to 30 amino acids.

Examples of relatively poorly conserved regions include positions 2 to 29, positions 34 to 39, positions 41 to 44, positions 46 to 52, positions 58 to 60, positions 70 to 73, positions 75 to 86, positions 111 to 117, and positions 142 to 149 of SEQ ID NO: 1. It thus appears that substitution, deletion, insertion and/or addition of one or several amino acid residues can be suitably made in these regions. The glutamic acid residues at positions 119 and 210 of SEQ ID NO: 1 appear to be directly associated with the catalytic site for xylanase activity. From the standpoint of prevention of decrease in xylanase activity, it is preferable that 10 amino acid residues on each side of the glutamic acid residues at positions 119 and 210 of SEQ ID NO: 1 remain unmutated; preferably 5 amino acid residues, more preferably 3 amino acid residues, still more preferably 2 amino acid residues, and particularly more preferably 1 amino acid residue on each side of the glutamic acid residues remains unmutated. An amino acid sequence selected from SEQ ID NOs: 1 to 7 may have a deletion of the first methionine.

Substitution, deletion, insertion, or addition of one or several amino acid residues may be made in any of the amino acid sequences of SEQ ID NOs: 1 to 7, but is preferably made in the amino acid sequence of, for example, SEQ ID NO: 1. It is known in the art how to make a mutation such as substitution, deletion, insertion, or addition of one or several amino acid residues of a specific amino acid sequence such as those of SEQ ID NOs: 1 to 7, and any technique can be used. Such a mutation can be made by using, for example, the restriction enzyme treatment, the treatment using exonuclease, DNA ligase, etc., directed mutagenesis, or random mutagenesis.

In the polypeptide (C), the amino acid sequence identity thereof to an amino acid sequence selected from SEQ ID NOs: 1 to 7 is preferably 80% or more, more preferably 85% or more, even more preferably 90% or more, further more preferably 93% or more, still more preferably 95% or more, even still more preferably 98% or more, and even still further more preferably 99% or more. In one embodiment, the polypeptide (c) preferably has the above degrees of identity to the amino acid sequence of SEQ ID NO: 1.

The amino acid sequence identity can be determined by using a commercially available analytical tool or an analytical tool available through telecommunication lines (Internet). For example, the amino acid sequence identity can be determined by using ClustalW Ver. 2.1 Pairwise Alignment (see the website clustalw.ddbj.nig.ac.jp/index.php?lang=ja) with default parameters. Alternatively, the amino acid sequence identity can be determined by using the BLAST (Basic Local Alignment Search Tool) homology algorithm available from of the National Center for Biotechnology Information (NCBI) at the website www.ncbi.nlm.nih.gov/BLAST/ with default parameters (default setting).

The polypeptide according to the present invention has xylanase activity, preferably with an optimum activity temperature of about 70° C., and it is preferable that the polypeptide exhibits sufficient activity at a temperature of about 40 to 80° C. As used herein, the term "sufficient activity" refers to 60% or more activity, and preferably 70% or more activity, when the activity at an optimum activity temperature is taken as 100%. The polypeptide according to the present invention preferably has an optimum pH of about 5 to 6.5.

The polypeptide according to the present invention can be produced in accordance with a genetic engineering procedure by using the later-described polynucleotide according to the present invention. The polypeptide according to the present invention can also be produced on the basis of the information of the amino acid sequences of SEQ ID NOs: 1 to 7 by using an ordinary protein chemical synthesis technique (e.g., liquid-phase method, and solid-phase method).

2. Polynucleotide

The polynucleotide according to the present invention encodes the polypeptide having xylanase activity described in section 1 above. A typical polynucleotide according to the present invention has a base sequence selected from SEQ ID NOs: 8 to 21. A polynucleotide having a base sequence selected from SEQ ID NOs: 8 and 9 encodes a polypeptide having the amino acid sequence of SEQ ID NO: 1. A polynucleotide having a base sequence selected from SEQ ID NOs: 10 and 11 encodes a polypeptide having the amino acid sequence of SEQ ID NO: 2. A polynucleotide having a base sequence selected from SEQ ID NOs: 12 and 13 encodes a polypeptide having the amino acid sequence of SEQ ID NO: 3. A polynucleotide having a base sequence selected from SEQ ID NOs: 14 and 15 encodes a polypeptide having the amino acid sequence of SEQ ID NO: 4. A polynucleotide having a base sequence selected from SEQ ID NOs: 16 and 17 encodes a polypeptide having the amino acid sequence of SEQ ID NO: 5. A polynucleotide having a base sequence selected from SEQ ID NOs: 18 and 19 encodes a polypeptide having the amino acid sequence of SEQ ID NO: 6. A polynucleotide having a base sequence selected from SEQ ID NOs: 20 and 21 encodes a polypeptide having the amino acid sequence of SEQ ID NO: 7. The base sequences of SEQ ID NOs: 8, 10, 12, 14, 16, 18, and 20 comprise no regions corresponding to introns. The base sequences of SEQ ID NOs: 9, 11, 13, 15, 17, 19, and 21 comprise regions corresponding to introns.

In the polynucleotide (c), the term "stringent conditions" refers to the conditions in which a "specific" hybrid is formed, and a "non-specific" hybrid is not formed. Specific examples of stringent conditions include: hybridization at 42° C., 1×SSC, and washing at 42° C. with a buffer fluid containing 0.1% SDS; preferably hybridization at 65° C., 0.1×SSC, and washing at 65° C. with a buffer fluid containing 0.1% SDS. Besides the temperature conditions, a variety of parameters that affect the stringency of hybridization are known, and one of ordinary skill in the art can suitably combine the parameters to enable stringency equivalent to the above-described stringency of hybridization.

DNAs hybridized under the above-described conditions include those having a stop codon generated in the middle and those that lost activity because of the mutagenesis of the active center. However, such DNAs can be avoided by using site-specific mutagenesis, or can be easily removed by measuring the enzyme activity with a known technique.

Polynucleotides hybridized under stringent conditions typically have homology of above a certain level to a polynucleotide used as a probe. The homology is, for example, 80% or more, preferably 85% or more, more preferably 90% or more, even more preferably 95% or more, even still more preferably 98% or more, and particularly more preferably 99% or more. To the base sequence of SEQ ID NO: 8, the base sequences of SEQ ID NOs: 9 to 21 have homology of 99% (SEQ ID NO: 9), 58% (SEQ ID NO: 10), 60% (SEQ ID NO: 11), 62% (SEQ ID NO: 12), 63% (SEQ ID NO: 13), 57% (SEQ ID NO: 14), 62% (SEQ ID NO: 15), 63% (SEQ ID NO: 16), 62% (SEQ ID NO: 17), 64% (SEQ ID NO: 18), 67% (SEQ ID NO: 19), 59% (SEQ ID NO: 20), and 61% (SEQ ID NO: 21). These percentages have been determined by using ClustalW (see the website clustalw.ddbj.nig.ac.jp/index.php?lang=ja) with default parameters.

The base sequence homology can be determined by using a commercially available analytical tool, or an analytical tool available through telecommunication lines (Internet). For example, software such as FASTA, BLAST, PSI-BLAST, or SSEARCH can be used to determine the homology. The major initial conditions typically applied to a BLAST search are specifically as follows. In Advanced BLAST 2.1, a blastn program is used, and the parameters are set to default values to perform a search. The homology value (%) of a nucleotide sequence is then calculated.

The polynucleotide according to the present invention is preferably present in an isolated state. As used herein, "DNA in an isolated state" means that the DNA is separated from components such as other nucleic acids and proteins that naturally accompany it. However, the DNA may contain a portion of other nucleic acid components, such as nucleic acid sequences that naturally flank the DNA sequence (e.g., the promoter region sequence and terminator sequence). DNAs prepared by a genetic engineering procedure, such as cDNA molecules, are, when in an isolated state, preferably substantially free of other components such as cell components and culture media. Likewise, in DNAs prepared by a chemical synthesis, "DNA in an isolated state" means that the DNA is substantially free of precursors (starting materials) such as dNTP, as well as chemical substances, etc., used in the synthetic process.

The polynucleotide according to the present invention can easily be prepared on the basis of the base sequence information of SEQ ID NOs: 8 to 21 by using a chemical DNA synthesis technique (e.g., phosphoramidite method) or a genetic engineering technique.

3. Expression Vector

The recombinant vector according to the present invention comprises the polynucleotide according to the present invention. The expression vector according to the present invention may further comprise, in addition to the polynucleotide of the present invention, polynucleotides that encode other proteins without particular limitation, as long as the expression of the polynucleotide of the present invention is possible.

The type of the vector is suitably selected according to the type of the host cell. Examples of vectors include plasmid vectors, cosmid vectors, phage vectors, and virus vectors (e.g., adenovirus vectors, retroviral vectors, and herpes viral vectors).

Examples of vectors that enable expression in *Escherichia coli* include pUC19, pUC18, pBR322, pHSG299, pHSG298, pHSG399, pHSG398, RSF1010, pMW119, pMW118, pMW219, pMW218, and pET. Examples of vectors that enable expression in yeast include pBR322, pJDB207, pSH15, pSH19, pYepSec1, pMFa, and pYES2. Examples of vectors that enable expression in insects include pAc and pVL.

For a eukaryotic host cell, suitably used expression vectors are those comprising, upstream of the polynucleotide to be expressed, a promoter, an RNA splicing site, a polyadenylation site, a transcription termination sequence, and the like. The expression vectors may further optionally comprise a replication origin, an enhancer, and/or a selection marker.

4. Transformant

The transformant according to the present invention is obtained by transformation with the above-described recombinant vector. The host cell used in transformation is not particularly limited as long as the polypeptide of the present invention can be produced, and either prokaryotic cells or eukaryotic cells can be used. Specific examples of host cells include prokaryotic cells including bacteria of genus *Escherichia coli* such as *Escherichia coli* (e.g., HB101, MC1061, JM109, CJ236, and MV1184), coryneform bacteria such as *Corynebacterium glutamicum*, actinomycetes such as bacteria of genus *Streptomyces*, bacteria of genus *Bacillus* such as *Bacillus subtilis*, bacteria of genus *Streptococcus*, and bacteria of genus *Staphylococcus*; yeast such as genus *Saccharomyces*, genus *Pichia*, and genus *Kluyveromyces*, and fungal cells such as genus *Aspergillus*, genus *Penicillium*, genus *Trichoderma*, and genus *Acremonium*; insect cells including *Drosophila* S2, *Spodoptera* Sf9, and silkworm-culturing cells; and plant cells. It is also possible to produce the polypeptide in a medium by exploiting the protein secretory capacity of *Bacillus subtilis*, yeast, *Aspergillus oryzae*, actinomycetes, and the like.

To introduce the recombinant expression vector into a host cell, a conventional method can be used. Examples include a variety of methods such as the competent cell method, the protoplast method, the electroporation method, the microinjection method, and the liposome fusion method. Specific examples of methods for introducing the recombinant expression vector into coryneform bacteria include, but are not limited to, the protoplast method (Gene, 39, 281-286, 1985) and the electroporation method (Bio/Technology, 7, 1067-1070, 1989).

The transformant according to the present invention is capable of producing the polypeptide of the present invention, and thus can be used for producing the polypeptide of the present invention. The transformant itself can also be used for producing xylose and/or xylooligosaccharides from a sample containing xylan.

5. Process for Producing Polypeptide Using Transformant

The polypeptide according to the present invention can be produced by culturing the transformant of the present invention, and collecting the polypeptide having xylanase activity from the culture. For culture, a passage culture or batch culture can be used with a medium suitable for the host cell. The culture can be carried out until a sufficient amount of the polypeptide is produced, with monitoring of the activity of the polypeptide produced inside and outside of the transformant as a guide.

The culture medium may be suitably selected from conventionally used media according to the host cell. The culture can be carried out under conditions suitable for growth of the host cell. Examples of media used for culturing *Escherichia coli* include nutrient media such as LB medium, and minimal media to which a carbon source, a nitrogen source, a vitamin source, and the like are added, such as M9 medium.

The culture conditions can also be suitably determined according to the type of the host cell. The culture is typically carried out at 16 to 42° C., preferably 25 to 37° C., for 5 to 168 hours, preferably for 8 to 72 hours. Depending on the host, either shaking culture or static culture can be used. Agitation may optionally be applied, and ventilation may optionally be provided. When an induction promoter is used for expressing xylanase, a promoter-inducing agent may be added to the medium to perform a culture.

Purification or isolation of xylanase from a culture supernatant can be carried out by suitably combining known techniques. Examples of techniques for use include ammonium sulfate precipitation, solvent precipitation (e.g., ethanol), dialysis, ultrafiltration, acid extraction, and a variety of chromatographic approaches (e.g., gel filtration chromatography, anion- or cation-exchange chromatography, phosphocellulose chromatography, hydrophobic interaction chromatography, affinity chromatography, hydroxyapatite chromatography, lectin chromatography, and high-performance liquid chromatography). Examples of carriers used in affinity chromatography include carriers to which an antibody against xylanase is bound, and carriers to which a substance with affinity for a peptide tag is bound, when the peptide tag is added to xylanase.

When xylanase is accumulated inside the host cells, the transformed cells are disrupted, and xylanase is purified or isolated from the centrifuged supernatant of the disrupted product by the techniques described above. For example, after completion of culture, the cells collected by centrifugation are suspended in a buffer for cell disruption (20 to 100 mM Tris-HCl (pH 8.0), 5 mM EDTA), and disrupted by ultrasonication. The disruption-treated fluid is centrifuged at 10,000 to 15,000 rpm for 10 to 15 minutes to thereby obtain a supernatant. The precipitation after centrifugation can optionally be solubilized with guanidinium chloride, urea, or the like, and then further purified.

The xylanase activity of the obtained polypeptide can be measured by a saccharification test using a xylan-containing biomass (e.g., bagasse) as a substrate. For example, the activity of the purified enzyme can be measured by the method disclosed in Bailey et al. (J. Biotech. 23, 1992, pp. 257-270).

6. Process for Producing Xylose/Xylooligosaccharides Using Polypeptide of the Present Invention The polypeptide having xylanase activity according to the present invention, when contacted with a sample containing xylan (e.g., biomass resources), decomposes the biomass resource to thereby produce molasses containing xylose and/or oligoxylose. When a biomass resource is used as a xylan-containing sample, molasses can be produced more efficiently by using the polypeptide of the present invention in combination with other enzymes such as cellulase.

The type of xylan-containing sample is not particularly limited, as long as the sample is decomposable by the polypeptide of the present invention. Examples of xylan-containing samples include bagasse, wood, bran, wheat straw, rice straw, chaff, soybean meal, soy pulp, coffee grounds, and rice bran. In the present invention, bagasse is preferable for use.

To produce molasses containing xylose and/or oligoxylose from a xylan-containing sample, a known method can be used. Biomass resources for use may be either dried materials or wet materials. The materials are preferably milled into particles of 100 to 1,000 μm in size beforehand to increase processing efficiency. Milling is performed by using a device such as a ball mill, a vibrational mill, a cutter mill, or a hammer mill. The milled biomass resource is suspended in an aqueous vehicle, and the xylanase of the present invention and cellulase are added thereto, followed by heating with stirring to thereby decompose or saccharize the biomass resource. The xylanase may be used singly, but is preferably added together with other enzymes such as cellulase to a sample from the standpoint of efficient decomposition of the biomass.

When the polypeptide of the present invention is contacted with a xylan-containing sample in an aqueous solution, the pH and the temperature of the reaction liquid can be suitably determined as long as the xylanase is not deactivated. Because of the relatively high optimum temperature and excellent temperature stability of the xylanase according to the present invention, it is preferable to carry out the reaction at or around the optimum temperature from the standpoint of efficient decomposition of the sample to obtain molasses. For example, the process according to the present invention can be carried out under ordinary pressure, a pH of 4 to 9, and a temperature of 5 to 90° C., preferably 15 to 80° C., more preferably 30 to 75° C., 50 to 70° C., or 50 to 65° C. There is no particular limitation to the amount of the polypeptide of the present invention to be added, and the amount can be within the range of, for example, 0.1 to 0.5% (w/w).

The molasses containing xylose and/or oligoxylose obtained by the process of the present invention may be used unmodified, or may be used as a dry product after removing water. It is also possible to further isomerize or decompose the molasses by a chemical reaction or enzymatic reaction depending on the intended use. The molasses or its fraction can be used, for example, as a starting material for alcohols such as methanol, ethanol, propanol, isopropanol, butanol, and butanediol by a fermentation process.

EXAMPLES

Example 1: Preparation of Xylanase

A polynucleotide comprising a base sequence of SEQ ID NO: 8 was introduced into an expression plasmid vector, pET11a, through a ligation reaction. A strain of *Escherichia coli*, *BL*21(DE3), was transformed by using this recombinant expression vector. The transformant was then inoculated into an LB medium containing 0.1 mg/mL of ampicillin, and grown in shake cultures at 37° C. until OD 0.6. After that, 0.1 mM of IPTG was added thereto, and the culture medium was shaken at 30° C. overnight, thereby inducing the expression of a protein. Upon completion of the culture, the cells were collected by centrifugation, and frozen at −20° C. The cells were then suspended and dissolved in 50 mL of 20 mM Tris-HCl at pH 8.0, followed by collection of a supernatant solution by centrifugation. The obtained supernatant was fractioned by anion chromatography (HiTrap Q HP column: GE Healthcare) eluting with a gradient of 0.0-1.0 M NaCl to thereby purify the polypeptide (XYLC-R1). The anion chromatography was carried out at a flow rate of 3 ml/min. The purified fraction was examined for the molecular weight and homogeneity by using SDS-PAGE (FIG. 1).

Figure 2:
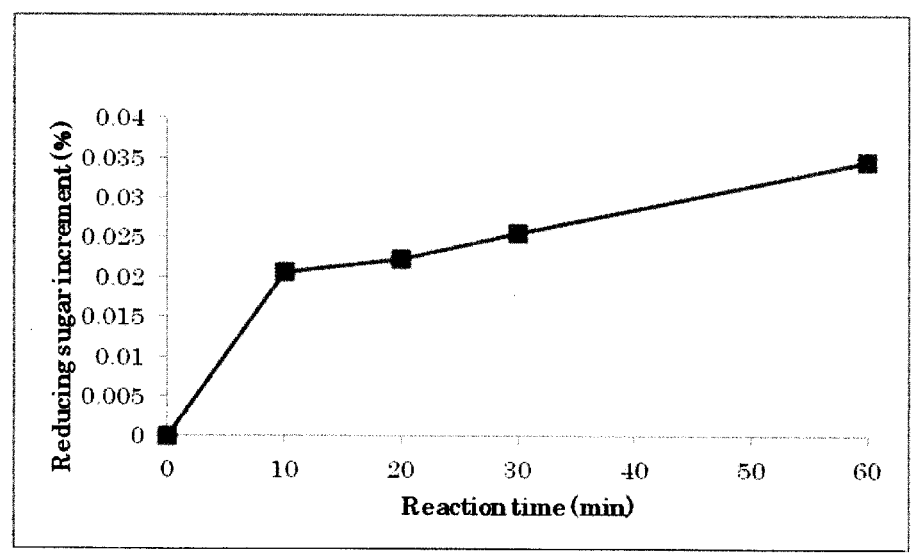
FIG. 2 shows the xylanase activity of the purified protein measured in Example 2.

Example 2: Measurement of Activity of Purified Protein 0.5 μM of the purified protein (XYLC-R1) and 0.5% by mass of xylan (final concentration each) were added to 50 mM of a sodium acetate buffer (pH 5.5), and an enzymatic reaction was started at 50° C. After the reaction was started, the reducing sugar concentration was measured at the 0-, 10-, 20-, 30-, and 60-minute point by the Somogyi-Nelson method (FIG. 2). As shown in FIG. 2, the results of the measurement revealed that a sufficient amount of reducing sugar was liberated, and that the purified protein was xylanase.

Example 3: Temperature Dependence of Enzyme Activity

Figure 3:
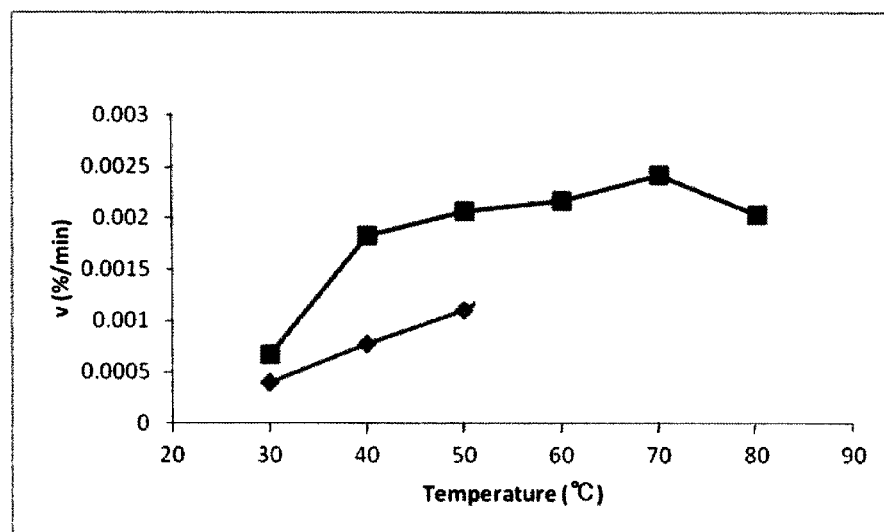
FIG. 3 shows the temperature dependence of xylanase measured in Example 3.

To examine the effects of the reaction temperature on the enzyme activity, the enzyme activity was measured in the same manner as in Example 2 by increasing the reaction temperature from 30° C. to 40° C., 50° C., 60° C., 70° C., and 80° C. As a comparable example, the activity of *Trichoderma*-derived xylanase of the same concentration was measured at a temperature in the range of 20 to 50° C. in the same manner. FIG. 3 shows the results (the symbols "■" and "◆" respectively indicate the xylanase purified in Example 1, and *Trichoderma*-derived xylanase). FIG. 3 reveals that the xylanase of the present invention has outstandingly higher activity than *Trichoderma*-derived xylanase in the temperature range in which the measurement was carried out.

Example 4: PH Dependence of Enzyme Activity

The effects of pH on xylanase activity of the enzyme that was confirmed to be xylanase in Example 2 was examined by using buffers at a pH of 3 to 10, and the optimum pH was found to be 5 to 6.5.

Examples 5: Crystallization of Enzyme Protein

Figure 4:
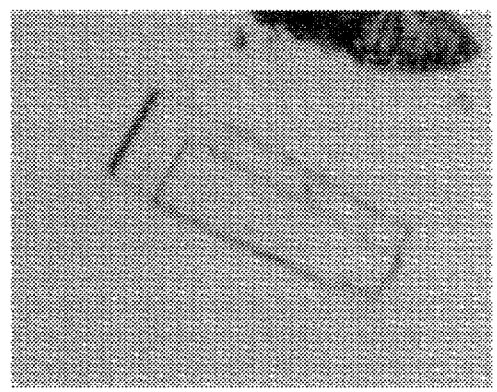
FIG. 4 shows a photographic image of xylanase crystallized by the hanging drop technique in Example 5.

The protein purified in Example 1 was crystallized by using the hanging drop technique under the following conditions: enzyme concentration (10 mg/mL); crystal mother liquor (0.8 M NaH2PO4, 0.8 M KH2PO4, 0.1 M BisTris pH 5.5); crystallization temperature (25° C.); and crystallization period (about 3 days). FIG. 4 shows a photographic image of the obtained crystal. From the absence of the electron density of about 10 to 13 amino acid residues residing in the N-terminal domain, it is inferred that these amino acid residues (about 10 to 13 amino acid residues residing in the N-terminal domain) are not essential for the structure and function of the enzyme.

Example 6: Crystal Structure Analysis of Enzyme Protein

Figure 5:
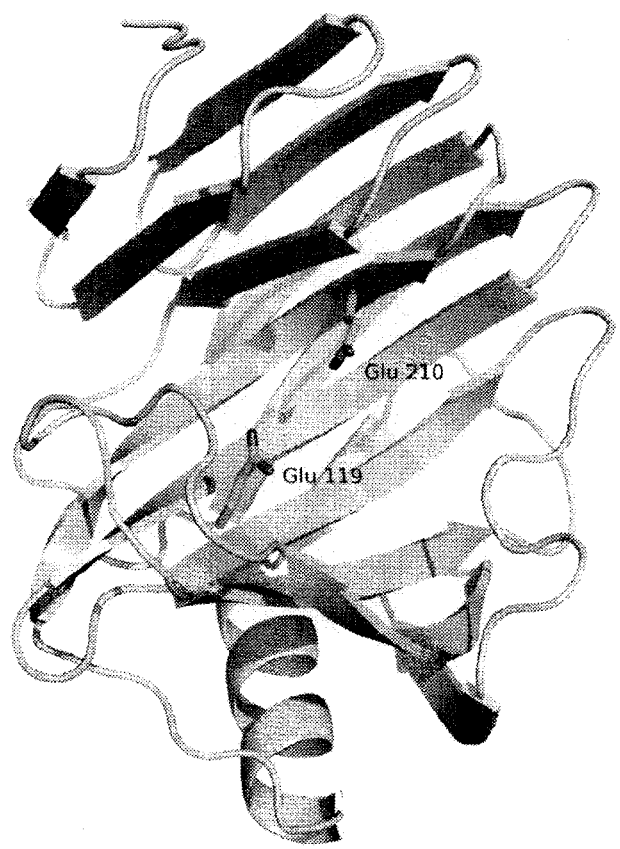
FIG. 5 shows a 3D-structure of xylanase according to the present invention obtained by a structural analysis.

At SPring8, collection and integration of the reflection points of an X-ray reflected by the enzyme crystal was implemented by using HKL2000, and then phasing was performed by molecular replacement using scaled data with a homologous protein as a model. After refinement, the structure of the xylanase was determined. The results of the structural analysis revealed the helix and β sheet structures. The results also identified the glutamic acid residues at positions 119 and 210 as the amino acid residues present in the catalytic site (FIG. 5).

Example 7: Identification of Other Xylanases

Based on the DNA sequence that encodes the protein (XYLC-R1) determined as xylanase in the above-described Example, homology searching was carried out to make a comparison with the genomic DNA of the organism from which the DNA of the protein is obtained. The homology search was carried out using the commercially available software in silico Molecular Cloning. A multiple alignment analysis was performed by using ClustalW Ver. 2 Multiple Alignment with default parameters. The results revealed that there are six more amino sequences that are speculated to be xylanase. FIG. 6 shows the alignment of these amino acid sequences. In FIG. 6, the symbol "*" denotes completely conserved amino acids; the symbol "•" denotes moderately conserved amino acids; and the symbol "••" denotes highly conserved amino acids. The amino acid sequence of XYLA is indicated by SEQ ID NO: 2; the amino acid sequence of XYLB is indicated by SEQ ID NO: 3; the amino acid sequence of XYLD is indicated by SEQ ID NO: 4; the amino acid sequence of XYLE is indicated by SEQ ID NO: 5; the amino acid sequence of XYLF is indicated by SEQ ID NO: 6 and the amino acid sequence of XYLG is indicated by SEQ ID NO: 7.

Examples 8: Confirmation of Xylanase Activity

As shown in the table below, primers for obtaining, from the genomic DNA, base sequences that encode the proteins speculated to constitute xylanases (XYLA, XYLB, XYLD, XYLE, XYLF, and XYLG) in Example 7 were designed.

TABLE 1

| Enzyme | Primer | Base Sequence | SEQ ID NO: |
| --- | --- | --- | --- |
| XYLA | Forward | ATTGTTAACAAGATGAAGATCACATCAGTGTTCG | 23 |
|  | Reverse | AATCCTGCAGGTTAAGATACAGTAACAGTGGCACTTC | 24 |
| XYLB | Forward | ATTGTTAACATCATGGGCATCTCATCTATTCTTC | 25 |
|  | Reverse | AATCCTGCAGGCTATTGGCACTGACTGTAGTAAGCGT | 26 |
| XYLC | Forward | ATTGTTAACAAGATGAAGCTCTCTCTGGCTGCAA | 27 |
|  | Reverse | AATCCTGCAGGCTAGGACACGGTGATGGTACTAGAAC | 28 |
| XYLD | Forward | ATTGTTAACAAGATGCGGTCATTTGCTCGCCTTGTC | 29 |
|  | Reverse | AATCCTGCAGGTCAGCTAACAGTAAAATCCAGGTAAC | 30 |
| XYLE | Forward | ATTGTTAACAAGATGATTTATTTCCCTCAGCTCATG | 31 |
|  | Reverse | AATCCTGCAGGCTATTGAGTGGCAGTCTGCTGGGCA | 32 |
| XYLF | Forward | ATTGTTAACAAGATGTTCTCTTTCAGTACTGCCTT | 33 |
|  | Reverse | AATCCTGCAGGCTACAAGCATTGATAGTAGTACGGGT | 34 |
| XYLG | Forward | ATTGATATCAAGATGGTTGCTTTCTCGAGCTTATTTAC | 35 |
|  | Reverse | AATCCTGCAGGGTCCAACATCAATGCTACTTACAGC | 36 |

These primers comprise a restriction enzyme site, HpaI (GTTAAC), or SbfI (CCTGCAGG), in a 5' end region. In accordance with an ordinary technique, polynucleotide fragments to encode XYLA, XYLB, XYLC, XYLD, XYLE, XYLF, and XYLG were amplified using the genomic DNA as a template with these primer sets. Each sequence was cleaved with HpaI or SbfI, and introduced into a plasmid having a restriction enzyme site (EcoRV-SbfI). Accordingly, seven recombinant plasmids for expressing the proteins were obtained.

The recombinant plasmids were individually incorporated non-homologously into chromosomes of a uracil-requiring strain of a microorganism by using the protoplast-PEG technique in accordance with a known method, thereby giving seven types of transformants. Each of the transformants was cultured in a medium containing 2% starch as a carbon source, thereby giving a culture fluid. The xylanase activity was observed in the same manner as in Example 2. Table 2 below shows the results.

TABLE 2

| Enzyme | Xylanase Activity In a Culture Fluid (U/mL) |
| --- | --- |
| XYLA | 98.12 |
| XYLB | 57.59 |
| XYLC | 1186 |
| XYLD | — |
| XYLE | 143.7 |
| XYLF | 103.67 |
| XYLG | 27.3 |

As seen in the results above, all of the proteins except for XYLD showed xylanase activity. Each of the recombinantly expressed proteins was homogeneously purified by column chromatography, and the N-terminal sequence of each protein was determined. This revealed that the recombinantly expressed proteins were the desired recombinase. Table 3 below shows the N-terminal sequence of each of the confirmed proteins.

TABLE 3

| Enzyme | N-terminal Sequence |
| --- | --- |
| XYLA | AGGIN (SEQ ID NO: 37) |
| XYLB | AEAIN (SEQ ID NO: 38) |
| XYLC | QSITT (SEQ ID NO: 39) |
| XYLE | ATNYI (SEQ ID NO: 40) |
| XYLF | NTPNS (SEQ ID NO: 41) |
| XYLG | SAINY (SEQ ID NO: 42) |

The invention claimed is:

1. A polypeptide having xylanase activity and comprising an amino acid sequence having at least 99% sequence identity with an amino acid sequence of SEQ ID NO:1, wherein the polypeptide does not have the amino acid sequence of SEQ ID NO: 1.

2. A polynucleotide selected from the group consisting of
   (a) a polynucleotide comprising a base sequence of SEQ ID NO:8; and
   (b) a polynucleotide having at lease 95% sequence identity with the base sequence of SEQ ID No:8 and that encodes a polypeptide having xylanase activity.

3. An expression vector comprising the polynucleotide according to claim 2.

4. A transformant obtained by transformation with the expression vector according to claim 3.

5. A process for producing xylanase, the process comprising the step of culturing the transformant according to claim 4.

6. A process for producing xylose and/or xylobiose, comprising:
   (a) preparing an isolated polypeptide having an amino acid sequence with at least 99% sequence identity with the amino acid sequence of SEQ ID NO:1 and that exhibits xylanase activity, and
   (b) allowing the polypeptide of (a) to act on a sample containing xylan.

* * * * *

SEQUENCE LISTING

<160> NUMBER OF SEQ ID NOS: 42

<210> SEQ ID NO 1
<211> LENGTH: 207
<212> TYPE: PRT
<213> ORGANISM: unknown
<220> FEATURE:
<223> OTHER INFORMATION: Xylanase

<400> SEQUENCE: 1

```
Met Phe Pro Ser Gly Leu Thr Gln His Ala Thr Gly Asp Leu Ser Lys
1               5                   10                  15

Arg Gln Ser Ile Thr Thr Ser Gln Thr Gly Thr Asn Asn Gly Tyr Tyr
            20                  25                  30

Tyr Ser Phe Trp Thr Asn Gly Gly Glu Val Thr Tyr Thr Asn Gly
        35                  40                  45

Asp Asn Gly Glu Tyr Ser Val Thr Trp Val Asn Cys Gly Asp Phe Thr
    50                  55                  60

Ser Gly Lys Gly Trp Asn Pro Ala Asn Ala Gln Thr Val Thr Tyr Ser
65                  70                  75                  80

Gly Glu Phe Asn Thr Ser Gly Asn Ala Tyr Leu Ala Val Tyr Gly Trp
                85                  90                  95

Thr Thr Asp Pro Leu Val Glu Tyr Tyr Ile Leu Glu Ser Tyr Gly Thr
            100                 105                 110

Tyr Asn Pro Ser Ser Gly Leu Thr Leu Leu Gly Gln Val Thr Ser Asp
        115                 120                 125

Gly Gly Thr Tyr Asp Ile Tyr Ser Thr Gln Arg Val Asp Gln Pro Ser
    130                 135                 140

Ile Glu Gly Thr Ser Thr Phe Asn Gln Tyr Trp Ser Val Arg Thr Glu
145                 150                 155                 160

Lys Arg Val Gly Gly Thr Val Thr Thr Ala Asn His Phe Ala Ala Trp
                165                 170                 175

Lys Ala Leu Gly Leu Glu Met Gly Thr Tyr Asn Tyr Met Ile Val Ser
            180                 185                 190

Thr Glu Gly Tyr Glu Ser Ser Gly Ser Ser Thr Ile Thr Val Ser
        195                 200                 205
```

<210> SEQ ID NO 2
<211> LENGTH: 209
<212> TYPE: PRT
<213> ORGANISM: unknown
<220> FEATURE:
<223> OTHER INFORMATION: xylanase

<400> SEQUENCE: 2

```
Met Lys Ile Thr Ser Val Phe Ala Gly Leu Leu Ala Thr Ala Leu Ala
1               5                   10                  15

Ala Pro Val Glu Asp Ser Ala Leu Val Glu Arg Ala Gly Gly Ile Asn
            20                  25                  30

Tyr Val Gln Asn Tyr Asn Gly Asn Leu Gly Asp Phe Thr Tyr Asn Glu
        35                  40                  45

Ser Ala Gly Thr Tyr Ser Met Tyr Trp Glu Asp Gly Val Asn Gly Asp
    50                  55                  60

Phe Val Val Gly Leu Gly Trp Ser Thr Gly Ala Ala Arg Ser Ile Thr
65                  70                  75                  80

Tyr Ser Ala Asn Tyr Asn Ala Ala Asn Ser Gly Ser Tyr Leu Ser Val
                85                  90                  95
```

```
Tyr Gly Trp Ile Asn Ser Pro Gln Ala Glu Tyr Ile Val Glu Asn
            100                 105                 110

Tyr Gly Asn Tyr Asn Pro Cys Ser Gly Ala Gln Ser Leu Gly Thr Leu
            115                 120                 125

Thr Ser Asp Gly Gly Thr Tyr Gln Val Cys Thr Asp Thr Arg Tyr Asn
130                 135                 140

Gln Pro Ser Ile Thr Gly Thr Ser Thr Phe Thr Gln Phe Phe Ser Val
145                 150                 155                 160

Arg Gln Asn Lys Arg Ser Ser Gly Thr Val Thr Thr Gly Asn His Phe
                165                 170                 175

Asn Phe Trp Ala Gln His Gly Phe Gly Asn Ser Tyr Asn Phe Gln Val
            180                 185                 190

Met Ala Val Glu Ala Phe Asn Gly Ala Gly Ser Ala Thr Val Thr Val
            195                 200                 205

Ser

<210> SEQ ID NO 3
<211> LENGTH: 282
<212> TYPE: PRT
<213> ORGANISM: unknown
<220> FEATURE:
<223> OTHER INFORMATION: xylanase

<400> SEQUENCE: 3

Met Gly Ile Ser Ser Ile Leu Leu Ser Ala Leu Ile Ala Gly Gly Ala
1               5                   10                  15

Leu Ala Leu Pro Ala Ala Glu Pro Val Ser Phe Asp Ile Arg Asp Glu
            20                  25                  30

Asn Ile Thr Leu Ala Arg Arg Ala Glu Ala Ile Asn Tyr Asn Gln Asn
        35                  40                  45

Tyr Ile Ala Ser Gly Ala Asn Val Gln Tyr Ser Pro Asn Ile Ala Ala
    50                  55                  60

Gly Ser Phe Ser Ile Asn Tyr Asn Thr Gln Gly Asp Phe Val Val Gly
65                  70                  75                  80

Leu Gly Trp Gln Pro Gly Asp Ala Asn Pro Ile Thr Tyr Ser Gly Ser
                85                  90                  95

Phe Ser Ala Ser Gly Val Gly Ile Leu Ala Val Tyr Gly Trp Thr Thr
            100                 105                 110

Asn Pro Leu Val Glu Tyr Tyr Ile Met Glu Val His Asp Gly Tyr Gln
            115                 120                 125

Thr Val Gly Thr His Lys Gly Thr Val Thr Ser Asp Gly Gly Thr Tyr
130                 135                 140

Asp Ile Trp Glu His Gln Gln Val Asn Gln Pro Ser Ile Leu Gly Thr
145                 150                 155                 160

Ser Thr Phe Asn Gln Tyr Ile Ser Ile Arg Gln Ser Pro Arg Thr Ser
                165                 170                 175

Gly Thr Val Thr Val Gln Asn His Phe Asn Ala Trp Ala Gln Ala Gly
            180                 185                 190

Leu Asn Leu Gly Thr Met Asn Tyr Gln Val Leu Ala Val Glu Ser Trp
            195                 200                 205

Ser Gly Ser Gly Ser Gly Gln Ile Ser Leu Ser Lys Gly Thr Gly Gly
            210                 215                 220

Gly Thr Thr Thr Thr Pro Thr Gly Pro Thr Ser Thr Ser Thr Ala
225                 230                 235                 240

Pro Ser Ser Gly Gly Thr Gly Ala Ala Gln Trp Gly Gln Cys Gly Gly
```

```
                        245                 250                 255

Ile Gly Trp Thr Gly Pro Thr Thr Cys Val Ser Pro Tyr Thr Cys Lys
            260                 265                 270

Tyr Phe Asn Ala Tyr Tyr Ser Gln Cys Gln
        275                 280

<210> SEQ ID NO 4
<211> LENGTH: 255
<212> TYPE: PRT
<213> ORGANISM: unknown
<220> FEATURE:
<223> OTHER INFORMATION: xylanase

<400> SEQUENCE: 4

Met Arg Ser Phe Ala Arg Leu Val Phe Ser Leu Leu Pro Val Ile Gly
1               5                   10                  15

Ala Leu Ala Val Pro Ala Thr Ser Asp Asn His Ala Arg Tyr Leu Asp
            20                  25                  30

Met Ala Ser Arg Ser Ala Asp Phe Arg Gln Arg Ile Arg Asp Met Ile
        35                  40                  45

Ala Asn Ala Thr Gln Glu Asn Asp Ile Ser Lys Arg Asp Ser Val Phe
    50                  55                  60

Ser Thr Ser Lys Asp Gly Val Asp Ser Ala Gly Phe Tyr Tyr Ser Leu
65                  70                  75                  80

Tyr Asn Asp Asn His Ala Ser Ala Gly Tyr Thr Glu Phe Ser Asp Ser
                85                  90                  95

Gly Arg Phe Glu Val Gly Trp Asn Leu Ala Ser Ser Ser Glu Phe Leu
            100                 105                 110

Gly Gly Lys Gly Tyr Arg Asp Thr Lys Thr Arg Cys Ser Leu Thr Trp
        115                 120                 125

Asp Gly Tyr Phe Thr Ala Thr Gly Asp Tyr Thr Leu Ala Ile Tyr Gly
    130                 135                 140

Trp Thr Leu Asn Pro Val Thr Glu Trp Tyr Ile Val Glu Gln His Gly
145                 150                 155                 160

Thr Gly Thr Pro Gly Asn Gly Asn Val Arg Gly Thr Ile Thr Ser Asp
                165                 170                 175

Gly Gly Thr Tyr Asp Val Tyr Asp Leu Tyr Tyr Ser Asn Val Pro Ser
            180                 185                 190

Ile Tyr Gly Val Thr Ser Phe His Gln Tyr Trp Ser Ile Arg Asn Val
        195                 200                 205

Gly Arg Ser Thr Gly Thr Val Asp Val Thr Lys His Phe Asp Thr Trp
    210                 215                 220

Lys Ser Leu Gly Leu Asn Pro Gly Thr Pro Ile Phe Gln Met Val Thr
225                 230                 235                 240

Leu Glu Gly Phe Lys Gly Gln Gly Tyr Leu Asp Phe Thr Val Ser
                245                 250                 255

<210> SEQ ID NO 5
<211> LENGTH: 234
<212> TYPE: PRT
<213> ORGANISM: unknown
<220> FEATURE:
<223> OTHER INFORMATION: xylanase

<400> SEQUENCE: 5

Met Ile Tyr Phe Pro Gln Leu Met Val Val Leu Thr Ala Ile His Ser
1               5                   10                  15
```

```
Ala Ile Ala Val Pro Thr Gly Gln Thr Gln Ala Ser Val Gln Lys Arg
            20                  25                  30

Gly Pro His Asn Phe Val Met Gly Pro Asp His Pro Leu Met Met Ala
        35                  40                  45

Arg Arg Asn Glu Ser Leu Phe Arg Arg Ala Thr Asn Tyr Ile Gln Asp
50                      55                  60

Tyr Thr Thr Gly Gly Thr Val Asp Phe Ser Pro Glu Ser Gly Glu Phe
65                      70                  75                  80

Ser Leu Ser Trp Asp Thr Asp Phe Val Val Gly Val Gly Trp
                85                  90                  95

Asn Pro Gly Ser Thr Glu Pro Ile Thr His Ser Gly Ser Phe Asn Val
            100                 105                 110

Glu Ser Gly Leu Ala Ser Leu Ser Val Tyr Gly Trp Thr Thr Asn Pro
        115                 120                 125

Leu Val Glu Tyr Tyr Ile Ile Asp Glu Tyr Val Asn Met Glu Gln Ala
    130                 135                 140

Gly Thr Gln Lys Gly Thr Val Tyr Ser Asp Gly Ala Thr Tyr Thr Ile
145                 150                 155                 160

Trp Glu Asn Gln Arg Val Asn Glu Pro Ser Ile Glu Gly Thr Ser Thr
                165                 170                 175

Phe Asn Gln Tyr Ile Ser Ile Arg Glu Ser Asn Arg Ala Ser Gly Thr
            180                 185                 190

Ile Thr Val Glu Asn His Phe Asn Ala Trp Ala Asn Val Gly Leu Lys
        195                 200                 205

Leu Gly Thr Met Asp Phe Gln Val Ile Ala Val Glu Ser Trp Asp Gly
    210                 215                 220

Ser Gly Asn Ala Gln Gln Thr Ala Thr Gln
225                 230

<210> SEQ ID NO 6
<211> LENGTH: 276
<212> TYPE: PRT
<213> ORGANISM: unknown
<220> FEATURE:
<223> OTHER INFORMATION: xylanase

<400> SEQUENCE: 6

Met Phe Ser Phe Ser Thr Ala Phe Phe Ala Ser Thr Leu Ala Ala Gly
1               5                   10                  15

Ile Leu Ala Ser Pro Ala Ala Ala Pro Ser Ala Leu Thr Lys Arg Asn
            20                  25                  30

Thr Pro Asn Ser Ser Gly Thr Asn Asn Gly Phe Phe Tyr Gln Phe Trp
        35                  40                  45

Asp Asp Gly Ser Ser Gly Thr Thr Thr Tyr Thr Asn Gly Pro Ala Gly
50                  55                  60

Glu Tyr Ser Val Asn Trp Gln Asn Val Gly Asp Phe Thr Ala Gly Lys
65                  70                  75                  80

Gly Trp Ser Gln Ala Glu Pro Arg Asn Ile Ser Phe Ser Gly Ser Val
                85                  90                  95

Asn Cys Gly Gly Asn Phe Tyr Leu Ala Val Tyr Thr Trp Ser Thr Gln
            100                 105                 110

Gly Glu Asn Tyr Ile Leu Glu Asp Tyr Gly Thr Tyr Asn Pro Cys Ser
        115                 120                 125

Gly Gly Thr Ser Lys Gly Ser Leu Tyr Ser Asp Gly Ser Glu Tyr Gln
    130                 135                 140
```

```
Val Cys Leu Val Asp Arg Gly Asn Asn Tyr Leu Gln Asn Trp Ser Val
145                 150                 155                 160

Arg Gln Asn Lys Arg Thr Ser Gly Thr Val Thr Thr Ala Asn His Tyr
            165                 170                 175

Asn Tyr Tyr Gln Ser Gln Gly Met Asn His Asn Pro Leu Ser Ser Ala
            180                 185                 190

Val Tyr Gln Ile Val Ser Thr Glu Gly Tyr Gly Ser Ser Gly Ser Ala
            195                 200                 205

Asp Ile Thr Val Ser Glu Ala Ser Pro Ser Thr Ser Ser Ser Ala Ser
            210                 215                 220

Thr Thr Ser Ser Thr Ser Pro Ala Thr Thr Ser Ser Ser Ser Gly Thr
225                 230                 235                 240

Gly Ala Ser Gln Trp Gly Gln Cys Gly Gly Ile Gly Trp Asn Gly Pro
            245                 250                 255

Thr Thr Cys Val Ser Pro Tyr Thr Cys Gln Gln Ile Asn Pro Tyr Tyr
            260                 265                 270

Tyr Gln Cys Leu
            275

<210> SEQ ID NO 7
<211> LENGTH: 233
<212> TYPE: PRT
<213> ORGANISM: unknown
<220> FEATURE:
<223> OTHER INFORMATION: xylanase

<400> SEQUENCE: 7

Met Val Ala Phe Ser Ser Leu Phe Thr Ala Leu Ala Ala Ile Ala Gly
1               5                   10                  15

Ser Leu Ala Ala Pro Ala Asp Leu Val Lys Asn Asp Asn Val Pro Asp
            20                  25                  30

Leu Gly Ser Arg Gly Pro Ser Asn Phe Val Ile Asp Thr Thr Asn Asn
            35                  40                  45

Thr Ser Leu Ala Arg Arg Ser Ala Ile Asn Tyr Asp Gln Asp Tyr Thr
50                  55                  60

Thr Gly Gly Thr Val Asn Tyr Tyr Ser Ser Thr Gly Phe Glu Val
65                  70                  75                  80

Thr Trp Asn Thr Gln Asp Asp Phe Val Val Gly Val Gly Trp Asn Pro
            85                  90                  95

Gly Ser Thr Thr Pro Ile Asn Phe Gly Gly Gln Phe Ser Val Ser Ser
            100                 105                 110

Gly Thr Gly Leu Leu Ser Val Tyr Gly Trp Ser Thr Ser Pro Leu Val
            115                 120                 125

Glu Tyr Tyr Ile Ile Glu Asp Tyr Ala Asn Pro Pro Ser Phe Gly Thr
            130                 135                 140

Gln Lys Gly Ser Leu Thr Ser Asp Gly Thr Tyr Ile Ile Trp Glu
145                 150                 155                 160

Asn Thr Arg Tyr Asn Glu Pro Ser Ile Gln Gly Thr Ser Thr Phe Asn
            165                 170                 175

Gln Tyr Ile Ser Val Arg Gln Ser Pro Arg Thr Glu Gly Thr Val Thr
            180                 185                 190

Val Gln Asn His Phe Asn Ala Trp Lys Asn Leu Gly Met Asn Leu Gly
            195                 200                 205

Thr Leu Asn Phe Gln Val Ile Ala Ala Glu Gly Trp Gly Gly Ser Gly
            210                 215                 220
```

Ser Ala Ser Tyr Ala Val Asn Asn Asn
225                 230

<210> SEQ ID NO 8
<211> LENGTH: 624
<212> TYPE: DNA
<213> ORGANISM: unknown
<220> FEATURE:
<223> OTHER INFORMATION: xylanase

<400> SEQUENCE: 8

| | | | | |
|---|---|---|---|---|
| atgtttccat | ctggacttac | tcaacacgct | acgggagatc | tcagcaagcg | tcaatcaatc | 60 |
| acgacgagcc | agactgggac | gaacaacggc | tactactact | cgttctggac | caacggcgga | 120 |
| ggagaagtca | cctacacaaa | tggtgacaat | ggcgaataca | gcgtgacctg | ggtcaattgc | 180 |
| ggtgacttta | catctggcaa | gggctggaat | ccagctaatg | cccagactgt | cacctactct | 240 |
| ggagaattta | atacctctgg | aaacgcttat | ctcgccgttt | acggttggac | aactgatcct | 300 |
| cttgtcgaat | actacatcct | ggagtcctac | ggtacatata | acccatcatc | tggccttaca | 360 |
| ttacttggcc | aggttactag | cgatggtggt | acgtacgata | tctactcaac | acagcgtgtc | 420 |
| gaccaaccct | ccatcgaggg | aacttccacc | ttcaatcagt | actggtcggt | tcgcacagag | 480 |
| aagcgagtcg | gcggaactgt | caccacggcc | aaccactttg | cagcatggaa | ggcacttgga | 540 |
| cttgaaatgg | gtacttataa | ctatatgatt | gtgtctacag | aaggctacga | gagcagtggt | 600 |
| tctagtacca | tcaccgtgtc | ctag | | | | 624 |

<210> SEQ ID NO 9
<211> LENGTH: 735
<212> TYPE: DNA
<213> ORGANISM: unknown
<220> FEATURE:
<223> OTHER INFORMATION: xylanase

<400> SEQUENCE: 9

| | | | | | | |
|---|---|---|---|---|---|---|
| atgaagctct | ctctggctgc | aattggcatt | tgcacaactg | ccgccgtcgc | ctttccatct | 60 |
| ggacttactc | aacacgctac | gggagatctc | agcaagcgtc | aatcaatcac | gacgagccag | 120 |
| actgggacga | caacggcta | ctactactcg | ttctggacca | acggcggagg | agaagtcacc | 180 |
| tacacaaatg | gtgacaatgg | cgaatacagc | gtgacctggg | tcaattgcgg | tgactttaca | 240 |
| tctggcaagg | gctggaatcc | agctaatgca | cagtaagttt | ctattttgt | tgtgttctaa | 300 |
| gcttatattt | tacatactca | catcggaatt | tgaaggactg | tcacctactc | tggagaattt | 360 |
| aatacctctg | gaaacgctta | tctcgccgtt | tacggttgga | caactgatcc | tcttgtcgaa | 420 |
| tactacatcc | tggagtccta | cggtacatat | aacccatcat | ctggccttac | attacttggc | 480 |
| caggttacta | gcgatggtgg | tacgtacgat | atctactcaa | cacagcgtgt | cgaccaaccc | 540 |
| tccatcgagg | gaacttccac | cttcaatcag | tactggtcgg | ttcgcacaga | gaagcgagtc | 600 |
| ggcggaactg | tcaccacggc | caaccacttt | gcagcatgga | aggcacttgg | acttgaaatg | 660 |
| ggtacttata | actatatgat | tgtgtctaca | gaaggctacg | agagcagtgg | ttctagtacc | 720 |
| atcaccgtgt | cctag | | | | | 735 |

<210> SEQ ID NO 10
<211> LENGTH: 630
<212> TYPE: DNA
<213> ORGANISM: unknown
<220> FEATURE:
<223> OTHER INFORMATION: xylanase

```
<400> SEQUENCE: 10
atgaagatca catcagtgtt cgcgggcctc ctagccacag cattggccgc ccccgtcgag      60
gactctgctt tggtggagcg cgcgggtggt attaactatg tccagaatta caatggtaac    120
cttggtgact tcacgtacaa tgagagtgca gggacttatt cgatgtactg ggaggacgga    180
gtcaatggag acttcgtcgt tggcttaggc tggagtactg gtgctgctcg ctccattacc    240
tactctgcaa actataatgc tgccaattct ggctcctacc tctcggttta ggctggata     300 aactctccac aggccgaata ctatatagtt gagaattatg caattacaa cccttgcagc     360 ggggctcaga gccttggtac ccttacctct gacggtggca cctaccaagt ctgcaccgac    420
actcgttaca accagccatc catcacggga acgagcacct tcacgcaatt cttctccgtt    480
cgacaaaaca agcgctcatc cggaactgtc acgactggca accatttcaa tttctgggcc    540
cagcatggct ttggcaactc atacaatttc caggtcatgg cagtggaggc attcaatggc    600
gcaggaagtg ccactgttac tgtatcttaa                                     630

<210> SEQ ID NO 11
<211> LENGTH: 689
<212> TYPE: DNA
<213> ORGANISM: unknown
<220> FEATURE:
<223> OTHER INFORMATION: xylanase

<400> SEQUENCE: 11
atgaagatca catcagtgtt cgcgggcctc ctagccacag cattggccgc ccccgtcgag      60
gactctgctt tggtggagcg cgcgggtggt attaactatg tccagaatta caatggtaac    120
cttggtgact tcacgtacaa tgagagtgca gggacttatt cgatgtactg ggaggacgga    180
gtcaatggag acttcgtcgt tggcttaggc tggagtactg gtgctgctcg gtaggttgcg    240
atttaaacgt atattcattt gcgcaatgcc agatctgacg tttataaagc tccattacct    300
actctgcaaa ctataatgct gccaattctg gctcctacct ctcggtttat ggctggataa    360
actctccaca ggccgaatac tatatagttg agaattatgg caattacaac ccttgcagcg    420
gggctcagag ccttggtacc cttacctctg acggtggcac ctaccaagtc tgcaccgaca    480
ctcgttacaa ccagccatcc atcacgggaa cgagcacctt cacgcaattc ttctccgttc    540
gacaaaacaa gcgctcatcc ggaactgtca cgactgcaa ccatttcaat ttctgggccc    600
agcatggctt tggcaactca tacaatttcc aggtcatggc agtggaggca ttcaatggcg    660
caggaagtgc cactgttact gtatcttaa                                      689

<210> SEQ ID NO 12
<211> LENGTH: 849
<212> TYPE: DNA
<213> ORGANISM: unknown
<220> FEATURE:
<223> OTHER INFORMATION: xylanase

<400> SEQUENCE: 12
atgggcatct catctattct tctctctgct ctgatcgcgg ggggagcctt ggctctgccc      60
gctgcagaac ctgtgtcgtt cgatatccgg gatgaaaaca tcaccctggc gcgccgcgct    120
gaggcgatca actacaacca aaactacatt gctagtggtg ccaatgttca atactcgccc    180
aacatcgctg cgggttcttt ctccatcaac tacaatacgc aggggacttt gtggtggga     240 cttggttggc aaccaggtga tgctaacccc atcacctaca cgccgccctt ctcggcctcg    300
ggtgttggta tccttgccgt gtacggctgg accaccaacc cgctcgtgga atactatatc    360
```

| | |
|---|---|
| atggaggttc acgacggata ccagactgtc ggcacacaca agggcactgt gacgagcgac | 420 |
| ggcggcacct atgatatctg ggagcaccag caggtcaatc agccgtccat tctgggcacc | 480 |
| tccaccttca accagtacat ctcgatccgc aaagccccc ggacgagcgg tacggttacc | 540 |
| gtgcagaacc acttcaatgc ctgggcgcag gcgggcttga atctcggcac aatgaactac | 600 |
| caggtcctgg cagtcgagag ctggagcggc agcggctctg acaaatctc gctcagcaag | 660 |
| ggcactggcg gtggcaccac caccaccaca cccacgggtc ccaccagcac gagcaccgct | 720 |
| ccttcgagcg gaggtaccgg tgctgctcaa tggggacaat gcggaggaat ggctggacc | 780 |
| ggcccgacta cctgcgtgtc cccttatact tgcaagtact ttaacgctta ctacagtcag | 840 |
| tgccaatag | 849 |

<210> SEQ ID NO 13
<211> LENGTH: 915
<212> TYPE: DNA
<213> ORGANISM: unknown
<220> FEATURE:
<223> OTHER INFORMATION: xylanase

<400> SEQUENCE: 13

| | |
|---|---|
| atgggcatct catctattct tctctctgct ctgatcgcgg ggggagcctt ggctctgccc | 60 |
| gctgcagaac ctgtgtcgtt cgatatccgg gatgaaaaca tcaccctggc gcgccgcgct | 120 |
| gaggcgatca actacaacca aaactacatt gctagtggtg ccaatgttca atactcgccc | 180 |
| aacatcgctg cgggttcttt ctccatcaac tacaatacgc agggggactt tgtggtggga | 240 |
| cttggttggc aaccaggtga tgctaagtaa gaacttccag ctcctgcttt ttatcacgat | 300 |
| aatttttcga ctcatactaa ttcgtactat agccccatca cctacagcgg ctccttctcg | 360 |
| gcctcgggtg ttggtatcct tgccgtgtac ggctggacca ccaacccgct cgtggaatac | 420 |
| tatatcatgg aggttcacga cggataccag actgtcggca cacaaggg cactgtgacg | 480 |
| agcgacggcg gcacctatga tatctgggag caccagcagg tcaatcagcc gtccattctg | 540 |
| ggcacctcca ccttcaacca gtacatctcg atccgccaaa gccccgac gagcggtacg | 600 |
| gttaccgtgc agaaccactt caatgcctgg gcgcaggcgg gcttgaatct cggcacaatg | 660 |
| aactaccagg tcctggcagt cgagagctgg agcggcagcg gctctggaca aatctcgctc | 720 |
| agcaagggca ctggcggtgg caccaccacc accacccca cgggtcccac cagcacgagc | 780 |
| accgctcctt cgagcggagg taccggtgct gctcaatggg gacaatgcgg aggaattggc | 840 |
| tggaccggcc cgactacctg cgtgtcccct tatacttgca agtactttaa cgcttactac | 900 |
| agtcagtgcc aatag | 915 |

<210> SEQ ID NO 14
<211> LENGTH: 765
<212> TYPE: DNA
<213> ORGANISM: unknown
<220> FEATURE:
<223> OTHER INFORMATION: xylanase

<400> SEQUENCE: 14

| | |
|---|---|
| atgcggtcat ttgctcgcct tgtctttct cttctccctg ttatcggtgc tctggcagta | 60 |
| ccagccacaa gtgacaacca tgcgagatat cttgacatgg catccagatc ggccgacttt | 120 |
| cgccagagaa ttagggatat gatcgccaat gcgacgcaag aaaatgatat cagcaagcgt | 180 |
| gatagcgtct tcagcactag caaggacggc gtagactcgg ccgggttta ttattcgctg | 240 |

```
tacaatgaca atcacgcttc tgctggttat accgagttta gcgatagcgg caggtttgaa      300
gtcggatgga acttagccag ttcgtctgag ttcctcggtg gtaaaggcta cagggacaca      360
aaaactcgct cccttacatg ggacggttac ttcaccgcta ccggcgacta taccctggcc      420
atttacggat ggacgttgaa tccagtcacc gaatggtata tcgtcgagca gcatggaacg      480
ggcacacctg gcaatggaaa tgttcgcggt actattacca gcgacggcgg aacctacgac      540
gtttacgacc tgtattattc taatgtgcct tcgatctatg gcgtaacttc cttccatcag      600
tactggtcta ttcgaaacgt cggccgcagc acaggtacgg tagatgtcac taaacacttt      660
gatacctgga agtcactagg tctcaatcct ggcaccccga ttttccaaat ggtcacttta      720
gaaggattca agggtcaggg ttacctggat tttactgtta gctga                     765

<210> SEQ ID NO 15
<211> LENGTH: 845
<212> TYPE: DNA
<213> ORGANISM: unknown
<220> FEATURE:
<223> OTHER INFORMATION: xylanase

<400> SEQUENCE: 15
atgcggtcat tgctcgcct tgtcttttct cttctccctg ttatcggtgc tctggcagta       60
ccagccacaa gtgacaacca tgcgagatat cttgacatgg catccagatc ggccgacttt      120
cgccagagaa ttagggatat gatcgccaat gcgacgcaag aaaatgatat cagcaagcgt      180
gatagcgtct tcagcactag caaggacggc gtagactcgg ccgggtttta ttattcgctg      240
tacaatgaca atcacgcttc tgctggttat accgagttta gcgatagcgg caggtttgaa      300
gtcggatgga acttagccag ttcgtctgag ttcctcggtg gtaaaggcta cagggacaca      360
aaaactcggt gtgtaacaat aaacctcctg cccttctgct ctcgttacag cttatcttcc      420
aaatgtgata gctaatcgtg tatctcagct cccttacatg ggacggttac ttcaccgcta      480
ccggcgacta taccctggcc atttacggat ggacgttgaa tccagtcacc gaatggtata      540
tcgtcgagca gcatggaacg ggcacacctg gcaatggaaa tgttcgcggt actattacca      600
gcgacggcgg aacctacgac gtttacgacc tgtattattc taatgtgcct tcgatctatg      660
gcgtaacttc cttccatcag tactggtcta ttcgaaacgt cggccgcagc acaggtacgg      720
tagatgtcac taaacacttt gatacctgga agtcactagg tctcaatcct ggcaccccga      780
ttttccaaat ggtcacttta gaaggattca agggtcaggg ttacctggat tttactgtta      840
gctga                                                                  845

<210> SEQ ID NO 16
<211> LENGTH: 705
<212> TYPE: DNA
<213> ORGANISM: unknown
<220> FEATURE:
<223> OTHER INFORMATION: xylanase

<400> SEQUENCE: 16
atgatttatt tccctcagct catggtggtg ctcaccgcca tccactcagc aatcgctgtt       60 cctacgggc agactcaggc atctgttcag aagcgcggcc tcataacttt gttatgggc       120 cctgaccatc ctttgatgat ggcccgtcgc aatgagtcgt tattccgtcg ggccacaaac      180
tatatccagg actatactac tggaggcacc gtagatttct cccccgaaag tggcgagttc      240
tcattgtcct gggatactac cgatgacttt gttgttggtg ttggctggaa cccgggaagc      300
actgagccta ttacccactc cggcagcttc aatgttgaat ctggacttgc aagtctttct      360
```

```
gtgtatggct ggacaacaaa tcctcttgtt gagtactaca tcatcgatga gtatgtgaac    420
atggagcagg ctggtacaca gaaaggcacg gtgtacagcg acggtgccac gtacaccatc    480
tgggagaatc agcgtgtcaa cgagccatcg atcgaaggca cttcgacctt caaccagtac    540
atctctatcc gcgaatcgaa tcgtgccagc ggcaccatta cggtgaaaaa ccatttcaac    600
gcttgggcga atgtgggttt gaaattgggc actatggatt ccaggtaat tgctgtcgag     660 agctgggatg gcagtggtaa tgcccagcag actgccactc aatag                   705
```

<210> SEQ ID NO 17
<211> LENGTH: 760
<212> TYPE: DNA
<213> ORGANISM: unknown
<220> FEATURE:
<223> OTHER INFORMATION: xylanase

<400> SEQUENCE: 17

```
atgatttatt ccctcagct catggtggtg ctcaccgcca tccactcagc aatcgctgtt      60
cctacggggc agactcaggc atctgttcag aagcgcggcc tcataactt tgttatgggc    120 cctgaccatc ctttgatgat ggcccgtcgc aatgagtcgt tattccgtcg gccacaaac    180 tatatccagg actatactac tggaggcacc gtagatttct cccccgaaag tggcgagttc    240
tcattgtcct gggatactac cgatgacttt gttgttggtg ttggctggaa cccgggaagc    300
actgagtaag aaagaacccct ctccctcacg ttccccccct tgactgatat cccattccag    360
gcctattacc cactccggca gcttcaatgt tgaatctgga cttgcaagtc tttctgtgta    420
tggctggaca acaaatcctc ttgttgagta ctacatcatc gatgagtatg tgaacatgga    480
gcaggctggt acacagaaag gcacggtgta cagcgacggt gccacgtaca ccatctggga    540
gaatcagcgt gtcaacgagc catcgatcga aggcacttcg accttcaacc agtacatctc    600
tatccgcgaa tcgaatcgtg ccagcggcac cattacggtg aaaaccatt tcaacgcttg     660 ggcgaatgtg ggtttgaaat tgggcactat ggatttccag gtaattgctg tcgagagctg    720
ggatggcagt ggtaatgccc agcagactgc cactcaatag                         760
```

<210> SEQ ID NO 18
<211> LENGTH: 831
<212> TYPE: DNA
<213> ORGANISM: unknown
<220> FEATURE:
<223> OTHER INFORMATION: xylanase

<400> SEQUENCE: 18

```
atgttctctt tcagtactgc ctttttgct tctacgcttg cagccggcat cctcgccagc      60
cctgcggcag caccctccgc acttaccaag cgcaataccc ccaactcatc aggcacgaac    120
aacggcttct tctaccaatt ctgggatgat ggctccagcg ggactactac ttacacaaat    180
gggcctgccg ggaatactc cgtgaactgg cagaatgttg tgattttac cgcaggtaag    240 ggctggtcac aggctgagcc caggaatatc agcttctctg gtagcgtcaa ctgtgggggt    300
aacttctacc ttgctgtata cacttggtca acccagggtg agaactatat tctcgaggac    360
tacggcacct acaatccgtg ctctggtggc acgagtaaag cagtctttta cagcgatggg    420
agcgagtacc aagtctgcct ggtcgaccgt ggcaacaact atctccagaa ctggtccgtc    480
cgccagaaca gcgtacctc tggcactgtt acaacggcaa accactacaa ttactaccag    540
tctcagggca tgaaccacaa cccacttagc agcgccgttt atcagattgt gtctaccgaa    600
```

```
ggctacggca gcagcggctc cgctgatatc actgtgagtg aggcttctcc atccacttcc      660
tcttctgcga gcaccacgag ctccacttcc cccgctacga cgagcagcag ctcaggcact      720
ggcgcttctc aatggggaca gtgcggtggt atcggctgga atggtcccac cacttgtgtt      780
tcgccttata cttgccagca aataaacccg tactactatc aatgcttgta g              831

<210> SEQ ID NO 19
<211> LENGTH: 952
<212> TYPE: DNA
<213> ORGANISM: unknown
<220> FEATURE:
<223> OTHER INFORMATION: xylanase

<400> SEQUENCE: 19
atgttctctt tcagtactgc cttttttgct tctacgcttg cagccggcat cctcgccagc       60
cctgcggcag caccctccgc acttaccaag cgcaataccc ccaactcatc aggcacgaac      120
aacggcttct tctaccaatt ctgtatgtac aatgctacca ttagttcaca atactcaaaa      180
tccttacggc tgacccaacg ttaagggggat gatggctcca gcgggactac tacttacaca      240
aatgggcctg ccggggaata ctccgtgaac tggcagaatg ttggtgattt taccgcaggt      300
aagggctggt cacaggctga gcccaggaat atcagcttct ctggtagcgt caactgtggg      360
ggtaacttct accttgctgt atacacttgg tcaacccagg gtgagaacta tgtgggtctt      420 cttttccagtc tgacgcaatg atatgtgact gcaatctgac ccaggataga ttctcgagga      480
ctacggcacc tacaatccgt gctctggtgg cacgagtaaa ggcagtcttt acagcgatgg      540
gagcgagtac caagtctgcc tggtcgaccg tggcaacaac tatctccaga actggtccgt      600
ccgccagaac aagcgtacct ctggcactgt tacaacggca aaccactaca attactacca      660
gtctcagggc atgaaccaca acccacttag cagcgccgtt tatcagattg tgtctaccga      720
aggctacggc agcagcggct ccgctgatat cactgtgagt gaggcttctc catccacttc      780
ctcttctgcg agcaccacga gctccacttc cccgctacg acgagcagca gctcaggcac      840
tggcgcttct caatggggac agtgcggtgg tatcggctgg aatggtccca ccacttgtgt      900
ttcgccttat acttgccagc aaataaaccc gtactactat caatgcttgt ag             952

<210> SEQ ID NO 20
<211> LENGTH: 702
<212> TYPE: DNA
<213> ORGANISM: unknown
<220> FEATURE:
<223> OTHER INFORMATION: xylanase

<400> SEQUENCE: 20
atggttgctt tctcgagctt atttactgcc cttgcagcca ttgccggctc actcgccgct       60
ccagcagatc tggtcaagaa cgataatgtc cctgacctcg gcagccgcgg ccctttcaaac      120 ttcgttatcg acacaacgaa caacacctcc ttggcccgtc gatcggcaat caactatgac      180
caggactata ccaccggcgg aacggtgaac tactattcct ccagcacggg gtttgaggtt      240
acctggaaca cgcaggacga tttcgtcgtt ggtgttggct ggaaccctgg ctctaccact      300
cccatcaact cggcggcca attctccgtc tccagcggca caggcctcct ctccgtctac      360
ggctggtcca cctcccccct cgtagaatac tacataatcg aagactacgc caacccaccc      420
agcttcggca cccaaaaggg ttccctgacc agcgacggcg gcacttacat catctgggag      480
aatacgcggt acaacgaacc ctcgattcag ggtacgtcga ctttcaatca gtatatttct      540
gtgcgccaga gtccccgtac ggagggcacg gttacggtgc agaatcattt taatgcttgg      600
```

```
aagaacttgg ggatgaattt ggggacgttg aattttcagg ttattgctgc cgaggggtgg      660
ggtgggagtg gttctgcttc gtatgctgtt aacaataact ag                        702
```

<210> SEQ ID NO 21
<211> LENGTH: 761
<212> TYPE: DNA
<213> ORGANISM: unknown
<220> FEATURE:
<223> OTHER INFORMATION: xylanase

<400> SEQUENCE: 21

```
atggttgctt tctcgagctt atttactgcc cttgcagcca ttgccggctc actcgccgct       60
ccagcagatc tggtcaagaa cgataatgtc cctgacctcg gcagccgcgg cccttcaaac      120
ttcgttatcg acacaacgaa caacacctcc ttggcccgtc gatcggcaat caactatgac      180
caggactata ccaccggcgg aacggtgaac tactattcct ccagcacggg gtttgaggtt      240
acctggaaca cgcaggacga tttcgtcgtt ggtgttggct ggaaccctgg ctctaccacg      300
taagccctct atctttccct tctatagtt taccaactga tagtctcctg gggaatagtc       360
ccatcaactt cggcggccaa ttctccgtct ccagcggcac aggcctcctc tccgtctacg      420
gctggtccac ctcccccctc gtagaatact acataatcga agactacgcc aacccaccca      480
gcttcggcac ccaaaagggt tccctgacca gcgacggcgg cacttacatc atctgggaga      540
atacgcggta caacgaaccc tcgattcagg gtacgtcgac tttcaatcag tatatttctg      600
tgcgccagag tccccgtacg gagggcacgg ttacggtgca gaatcatttt aatgcttgga      660
agaacttggg gatgaatttg gggacgttga attttcaggt tattgctgcc gaggggtggg      720
gtgggagtgg ttctgcttcg tatgctgtta acaataacta g                         761
```

<210> SEQ ID NO 22
<211> LENGTH: 223
<212> TYPE: PRT
<213> ORGANISM: unknown
<220> FEATURE:
<223> OTHER INFORMATION: xylanase

<400> SEQUENCE: 22

```
Met Lys Leu Ser Leu Ala Ala Ile Gly Ile Cys Thr Thr Ala Ala Val
1               5                   10                  15

Ala Phe Pro Ser Gly Leu Thr Gln His Ala Thr Gly Asp Leu Ser Lys
            20                  25                  30

Arg Gln Ser Ile Thr Thr Ser Gln Thr Gly Thr Asn Asn Gly Tyr Tyr
        35                  40                  45

Tyr Ser Phe Trp Thr Asn Gly Gly Glu Val Thr Tyr Thr Asn Gly
    50                  55                  60

Asp Asn Gly Glu Tyr Ser Val Thr Trp Val Asn Cys Gly Asp Phe Thr
65                  70                  75                  80

Ser Gly Lys Gly Trp Asn Pro Ala Asn Ala Gln Thr Val Thr Tyr Ser
                85                  90                  95

Gly Glu Phe Asn Thr Ser Gly Asn Ala Tyr Leu Ala Val Tyr Gly Trp
            100                 105                 110

Thr Thr Asp Pro Leu Val Glu Tyr Tyr Ile Leu Glu Ser Tyr Gly Thr
        115                 120                 125

Tyr Asn Pro Ser Ser Gly Leu Thr Leu Leu Gly Gln Val Thr Ser Asp
    130                 135                 140

Gly Gly Thr Tyr Asp Ile Tyr Ser Thr Gln Arg Val Asp Gln Pro Ser
```

```
                145                 150                 155                 160
Ile Glu Gly Thr Ser Thr Phe Asn Gln Tyr Trp Ser Val Arg Thr Glu
                    165                 170                 175

Lys Arg Val Gly Gly Thr Val Thr Thr Ala Asn His Phe Ala Ala Trp
            180                 185                 190

Lys Ala Leu Gly Leu Glu Met Gly Thr Tyr Asn Tyr Met Ile Val Ser
        195                 200                 205

Thr Glu Gly Tyr Glu Ser Ser Gly Ser Ser Thr Ile Thr Val Ser
    210                 215                 220

<210> SEQ ID NO 23
<211> LENGTH: 34
<212> TYPE: DNA
<213> ORGANISM: Artificial sequence
<220> FEATURE:
<223> OTHER INFORMATION: Primer

<400> SEQUENCE: 23
attgttaaca agatgaagat cacatcagtg ttcg                           34

<210> SEQ ID NO 24
<211> LENGTH: 37
<212> TYPE: DNA
<213> ORGANISM: Artificial Sequence
<220> FEATURE:
<223> OTHER INFORMATION: Primer

<400> SEQUENCE: 24
aatcctgcag gttaagatac agtaacagtg gcacttc                        37

<210> SEQ ID NO 25
<211> LENGTH: 34
<212> TYPE: DNA
<213> ORGANISM: Artificial Sequence
<220> FEATURE:
<223> OTHER INFORMATION: Primer

<400> SEQUENCE: 25
attgttaaca tcatgggcat ctcatctatt cttc                           34

<210> SEQ ID NO 26
<211> LENGTH: 37
<212> TYPE: DNA
<213> ORGANISM: Artificial Sequence
<220> FEATURE:
<223> OTHER INFORMATION: Primer

<400> SEQUENCE: 26
aatcctgcag gctattggca ctgactgtag taagcgt                        37

<210> SEQ ID NO 27
<211> LENGTH: 34
<212> TYPE: DNA
<213> ORGANISM: Artificial Sequence
<220> FEATURE:
<223> OTHER INFORMATION: Primer

<400> SEQUENCE: 27
attgttaaca agatgaagct ctctctggct gcaa                           34

<210> SEQ ID NO 28
<211> LENGTH: 37
<212> TYPE: DNA
<213> ORGANISM: Artificial Sequence
```

<220> FEATURE:
<223> OTHER INFORMATION: Primer

<400> SEQUENCE: 28
aatcctgcag gctaggacac ggtgatggta ctagaac          37

<210> SEQ ID NO 29
<211> LENGTH: 36
<212> TYPE: DNA
<213> ORGANISM: Artificial Sequence
<220> FEATURE:
<223> OTHER INFORMATION: Primer

<400> SEQUENCE: 29
attgttaaca agatgcggtc atttgctcgc cttgtc           36

<210> SEQ ID NO 30
<211> LENGTH: 37
<212> TYPE: DNA
<213> ORGANISM: Artificial Sequence
<220> FEATURE:
<223> OTHER INFORMATION: Primer

<400> SEQUENCE: 30
aatcctgcag gtcagctaac agtaaaatcc aggtaac          37

<210> SEQ ID NO 31
<211> LENGTH: 36
<212> TYPE: DNA
<213> ORGANISM: Artificial Sequence
<220> FEATURE:
<223> OTHER INFORMATION: Primer

<400> SEQUENCE: 31
attgttaaca agatgattta tttccctcag ctcatg           36

<210> SEQ ID NO 32
<211> LENGTH: 36
<212> TYPE: DNA
<213> ORGANISM: Artificial Sequence
<220> FEATURE:
<223> OTHER INFORMATION: Primer

<400> SEQUENCE: 32
aatcctgcag gctattgagt ggcagtctgc tgggca           36

<210> SEQ ID NO 33
<211> LENGTH: 35
<212> TYPE: DNA
<213> ORGANISM: Artificial Sequence
<220> FEATURE:
<223> OTHER INFORMATION: Primer

<400> SEQUENCE: 33
attgttaaca agatgttctc tttcagtact gcctt            35

<210> SEQ ID NO 34
<211> LENGTH: 37
<212> TYPE: DNA
<213> ORGANISM: Artificial Sequence
<220> FEATURE:
<223> OTHER INFORMATION: Primer

<400> SEQUENCE: 34
aatcctgcag gctacaagca ttgatagtag tacgggt          37

```
<210> SEQ ID NO 35
<211> LENGTH: 38
<212> TYPE: DNA
<213> ORGANISM: Artificial Sequence
<220> FEATURE:
<223> OTHER INFORMATION: Primer

<400> SEQUENCE: 35
attgatatca agatggttgc tttctcgagc ttatttac                              38

<210> SEQ ID NO 36
<211> LENGTH: 36
<212> TYPE: DNA
<213> ORGANISM: Artificial Sequence
<220> FEATURE:
<223> OTHER INFORMATION: Primer

<400> SEQUENCE: 36
aatcctgcag ggtccaacat caatgctact tacagc                                36

<210> SEQ ID NO 37
<211> LENGTH: 5
<212> TYPE: PRT
<213> ORGANISM: unknown
<220> FEATURE:
<223> OTHER INFORMATION: N-terminal Seqeunce

<400> SEQUENCE: 37

Ala Gly Gly Ile Asn
1               5

<210> SEQ ID NO 38
<211> LENGTH: 5
<212> TYPE: PRT
<213> ORGANISM: Unknown
<220> FEATURE:
<223> OTHER INFORMATION: N-terminal sequence

<400> SEQUENCE: 38

Ala Glu Ala Ile Asn
1               5

<210> SEQ ID NO 39
<211> LENGTH: 5
<212> TYPE: PRT
<213> ORGANISM: Unknown
<220> FEATURE:
<223> OTHER INFORMATION: N-termianl seqeunce

<400> SEQUENCE: 39

Gln Ser Ile Thr Thr
1               5

<210> SEQ ID NO 40
<211> LENGTH: 5
<212> TYPE: PRT
<213> ORGANISM: Unknown
<220> FEATURE:
<223> OTHER INFORMATION: N-terminal sequence

<400> SEQUENCE: 40

Ala Thr Asn Tyr Ile
1               5

<210> SEQ ID NO 41
<211> LENGTH: 5
```

```
<212> TYPE: PRT
<213> ORGANISM: Unknown
<220> FEATURE:
<223> OTHER INFORMATION: N-terminal sequence

<400> SEQUENCE: 41

Asn Thr Pro Asn Ser
1               5

<210> SEQ ID NO 42
<211> LENGTH: 5
<212> TYPE: PRT
<213> ORGANISM: Unknown
<220> FEATURE:
<223> OTHER INFORMATION: N-terminal sequence

<400> SEQUENCE: 42

Ser Ala Ile Asn Tyr
1               5
```